(12) United States Patent
Fernández Ledesma et al.

(10) Patent No.: US 11,142,734 B2
(45) Date of Patent: Oct. 12, 2021

(54) DEVICE AND MICROFLUIDIC SYSTEM FOR STUDYING CELL CULTURES

(71) Applicants: Universidad de Zaragoza, Saragossa (ES); Centro De Investigacion Biomedica En Red (CIBER), Madrid (ES)

(72) Inventors: Luis J. Fernández Ledesma, Saragossa (ES); Rosa Monge Prieto, Saragossa (ES); Guillermo Llamazares Prieto, Saragossa (ES); José María Ayuso Domínguez, Saragossa (ES); María Virumbrales Muñoz, Saragossa (ES); Jorge Santolaria Mazo, Saragossa (ES); Ignacio Ochoa Garrido, Madrid (ES)

(73) Assignees: UNIVERSIDAD DE ZARAGOZA, Saragossa (ES); CENTRO DE INVESTIGACIÓN BIOMÉDICA EN RED (CIBER), Madrid (ES)

( * ) Notice: Subject to any disclaimer, the term of this patent is extended or adjusted under 35 U.S.C. 154(b) by 346 days.

(21) Appl. No.: 15/774,254

(22) PCT Filed: Nov. 4, 2016

(86) PCT No.: PCT/ES2016/070782
§ 371 (c)(1),
(2) Date: May 7, 2018

(87) PCT Pub. No.: WO2017/077163
PCT Pub. Date: May 11, 2017

(65) Prior Publication Data
US 2018/0327701 A1    Nov. 15, 2018

(30) Foreign Application Priority Data
Nov. 6, 2015   (ES) .............................. ES201531607

(51) Int. Cl.
*B01L 3/00* (2006.01)
*C12M 1/32* (2006.01)
(Continued)

(52) U.S. Cl.
CPC .......... *C12M 23/16* (2013.01); *B01L 3/5027* (2013.01); *C12M 23/12* (2013.01); *C12M 29/10* (2013.01); *C12M 23/34* (2013.01)

(58) Field of Classification Search
None
See application file for complete search history.

(56) References Cited

U.S. PATENT DOCUMENTS 10,673,347 B2    6/2020   Sarnago Andía et al.
2005/0260745 A1  11/2005  Domansky et al.
(Continued)

FOREIGN PATENT DOCUMENTS

WO    2014/210207 A1   12/2014

OTHER PUBLICATIONS

Hattori et al., Integrated perfusion culture micro-chamber array chip for high-throughput drug dose response assay, 2010, 14th International Conference on Miniaturized Systems for Chemistry and Life Sciences (Year: 2010).*
(Continued)

*Primary Examiner* — Holly Kipouros
(74) *Attorney, Agent, or Firm* — Seed IP Law Group LLP

(57) ABSTRACT

The present invention relates to a novel microfluidic device and a microfluidic system for culturing cell samples based on: one or more culture wells (2) forming cell housing volumes for three-dimensional cell culture; one or more capillary channels (1) for circulating cells and/or fluid media, said channels (1) being connected to the wells (2) as well perfusion means; and an inlet port (3) and an outlet port (3') for seeding cells and/or for circulating fluid in said (Continued)

channel (1), said ports (3, 3') being connected to the ends of each capillary channel (1). The novel configuration of the ports (3, 3') and their corresponding channels (1) allows known microfluidic perfusion media to be improved, dispensing with the use of complex elements for injecting the fluid media, such as syringe pumps, for example. The invention also allows two-dimensional and three-dimensional culture studies to be performed simultaneously.

10 Claims, 4 Drawing Sheets

(51) Int. Cl.
*C12M 1/00* (2006.01)
*C12M 3/06* (2006.01)

(56) References Cited

U.S. PATENT DOCUMENTS

| | | | |
|---|---|---|---|
| 2008/0085556 A1* | 4/2008 | Graefing | C12M 21/06 435/383 |
| 2011/0236970 A1* | 9/2011 | Larsen | C12M 23/12 435/348 |
| 2012/0003732 A1 | 1/2012 | Hung et al. | |
| 2016/0194588 A1* | 7/2016 | Guenat | C12M 35/08 435/305.1 |
| 2017/0145362 A1* | 5/2017 | Ito | C12M 23/12 |
| 2018/0187261 A1 | 7/2018 | Garcia Gimenez et al. | |
| 2018/0320138 A1 | 11/2018 | Segovia Sanz et al. | |
| 2019/0366365 A1 | 12/2019 | Santamaría Ramiro et al. | |

OTHER PUBLICATIONS

Yoshimitsu et al., Microfluidic perfusion culture of human pluripotent stem cells under fully defined culture conditions, 2014, Biotechnology and Bioengineering, vol. 11 No. 5 (Year: 2014).*

U.S. Appl. No. 16/867,960, filed May 6, 2020.

Cimetta et al., "Micro-bioreactor arrays for controlling cellular environments: Design principles for human embryonic stem cell applications," *Methods* 47:81-89, 2009.

Inamdar et al., "Microfluidic cell culture models for tissue engineering," *Current Opinion in Biotechnology* 22:681-689, 2011.

Kim et al., "3D spherical microtissues and microfluidic technology for multi-tissue experiments and analysis," *Journal of Biotechnology* 205:24-35, 2015.

* cited by examiner

DEVICE AND MICROFLUIDIC SYSTEM FOR STUDYING CELL CULTURES

FIELD OF THE INVENTION

The present invention is comprised in the field of microfluidic systems for studying cell samples, for both surface culture samples and samples in culture volumes. More specifically, the invention relates to a chip-type microfluidic device and a microfluidic system that are equipped with culture wells, and rapid filling means for rapidly filling the wells through capillary forces.

BACKGROUND OF THE INVENTION

Different "lab-on-a-chip"-type cell culture and analysis systems based on microfluidic circuits comprising a plurality of microchannels for circulating cells and the corresponding culture media, as well as various chambers for culturing and monitoring said cells, are known today.

United States patent application US 2012/0003729 A1 describes an example of the mentioned systems. Said document relates to a microfluidic chip device (also referred to as "bioreactor") for culturing and maintaining living systems, comprising a channel configuration allowing perfusate flow with diffusional exchange to cultured tissue cells, but limiting cell migration. For this purpose, the chip comprises a layer arrangement configured to generate at least one channel inside said chip for receiving cells and liquid media, and a housing chamber located outside said channel intended for culturing cell samples. The layers of the device can be formed with materials such as glass, Mylar, PDMS, silicon, polymers, semiconductor materials, or any combination thereof.

Likewise, the described device comprises a porous barrier allowing fluid communication between the receiving channel and the culture chamber. Said barrier can be formed, for example, as a succession of partitions, to prevent or allow the passage of specific cells from the channel to the volume of the culture chamber. In turn, the channel can also be provided with a biocompatible coating layer which improves cell adhesion to the channel walls, promoting cell organization and the growth of cells that have been introduced, thereby generating cultures that are located on the volume immediately thereabove as it is formed by the three-dimensional culture chamber.

In order to use the cell culture systems of the state of the art like the one described in patent document US 2012/0003729 A1, there is a need to equip said systems with perfusion means for introducing cells and culture media which are usually based on the use of pumps or syringes applied at the microfluidic inlets configured for that purpose. Nevertheless, said need entails a limitation in the use of the culture systems since the mentioned perfusion means require long periods of filling and of introducing a flow into the microfluidic circuit that are extremely slow and thereby limit system performance. This drawback is magnified in greatly miniaturized equipment comprising a large number of culture chips, since the filling times are directly proportional to the number of chambers of said chips. The known perfusion pumps and syringes therefore constitute an obstacle to the operative efficiency of the known systems used to date, so there is a need to find new filling systems that overcome this drawback.

Additionally, the known culture systems are preferably intended for studying surface samples (for example, cells seeded on a planar substrate to a greater or lesser extent), also referred to as two-dimensional (2D) samples, or for studying said samples in culture volumes, also referred to as three-dimensional (3D) samples. Nevertheless, equipment which allows holding and studying both types of cultures simultaneously using one and the same design are unheard of.

In order to solve these problems of the state of the art (i.e., the very long channel perfusion times of the microfluidic system, and the impossibility to analyze 2D and 3D samples using one and the same design), the present invention contemplates a novel microfluidic system that relies on capillarity-based rapid filling means, the design and technical elements of which furthermore allow culturing and studying both surface cell samples and cell samples in a culture volume.

BRIEF DESCRIPTION OF THE INVENTION

According to the information set forth in the preceding section, an object of the present invention is therefore to obtain cell culture devices which improve the perfusion means of systems of the state of the art, dispensing with the use of complex elements for injecting fluid media (for example, syringe pumps). Likewise, another object of the invention is to obtain cell culture devices and systems which allow studying two-dimensional and three-dimensional cultures simultaneously.

Said object is preferably achieved by means of a microfluidic device for culturing cell samples comprising:
- one or more culture wells forming cell housing volumes for three-dimensional cell culture;
- one or more capillary channels for circulating cells and/or fluid media, said channels being connected to the wells as well perfusion means; and
- an inlet port and an outlet port for seeding cells and/or for circulating fluid in said channels, said ports being connected to the ends of each capillary channel.

Advantageously, the ports of the device comprise housing volumes for housing a liquid at a level different from the level of the capillary channels, said volumes acting like pressure cylinders on said channels. Additionally, the device also comprises an upper region for accessing the wells, providing a two-dimensional cell culture surface adjacent to the wells.

As a result of this specially contrived design, complete perfusion of a fluid by means of capillary forces is achieved through the contact of said fluid with the fluid inlets of the device. In other words, the device is automatically filled when a drop of liquid is deposited in any of the fluid inlet ports. Therefore the filling of the device is not the result of any special perfusion protocol, but rather a result of capillary forces that are sufficient to perfuse the matrix of open microwells of the device, filling them with the desired culture medium.

In a preferred embodiment of the invention, the inlet and outlet ports of the channels have an opening in which a pipette and a fluid connector can be fitted. This leads to a versatile means that allows both cell seeding and fluid circulation for putting the device into operation.

In another preferred embodiment of the invention, the inlet ports of the device have a housing volume of at least 25 µl. More preferably, the channels follow a curved trajectory in the device and their cross-section has a diameter comprised between 300 and 500 microns. This leads to a configuration that enhances the generation of capillary forces in the channels, thereby reducing the times required for loading fluids in the device, compared with other alternatives of the state of the art.

In another preferred embodiment of the invention, each capillary channel communicates several culture wells, said culture wells being distributed in rows. The perfusion of a plurality of said culture wells can thereby be performed by means of circulating cells or fluid through said channel.

In another preferred embodiment of the invention, the device comprises one or more walls confining the perimeter of the upper region for maintaining fluids in said region. This allows providing housing means for two-dimensional cultures (i.e., distributed on the surface of the upper region), communicated with the wells of the device.

Another object of the present invention relates to a microfluidic system for studying cell cultures comprising a device according to any of the embodiments described herein, in combination with a closure cover for enclosing the upper region of said device, the device and cover being coupled together like independent parts. This allows configuring the aforementioned device as a lower part containing the lower channels through which a fluid suspension (for example, a hydrogel) will circulate, in addition to wells that will allow said fluid to access the surface of the device. In turn, the cover acting as an upper part sometimes works as the lid of the system, separating the culture surface generated by the hydrogel and the upper surface of the lower part. Cavities which will allow the formation of independent channels for each line of wells are preferably arranged in this upper part.

In a preferred embodiment of the invention, the closure cover of the system comprises a plurality of fluidic capillary channels, the layout of which coincides with the distribution of the wells of the microfluidic device. More preferably, a plurality of fluidic inlet and outlet ports connected to each channel, wherein the ports comprise housing volumes for housing a liquid at a level different from the level of the capillary channels, said volumes acting like pressure cylinders on said channels. In other words, both the device of the invention and its closure cover use analogous loading ports.

When the two parts are attached together (i.e., when the closure cover is placed over the microfluidic device), the channels are physically demarcated, being separated from one another. Two-dimensional cultures of a cell suspension can be seeded in this position on the surface demarcated by each channel which in turn comprises each row of wells containing a fluid.

The fluidic inlets of the upper part can act as a culture medium reservoir which allows renewing the culture medium by gravity. Likewise, connection through a connector to an external fluidic system which allows generating a flow through each channel in the system is also possible.

Figure 1A:
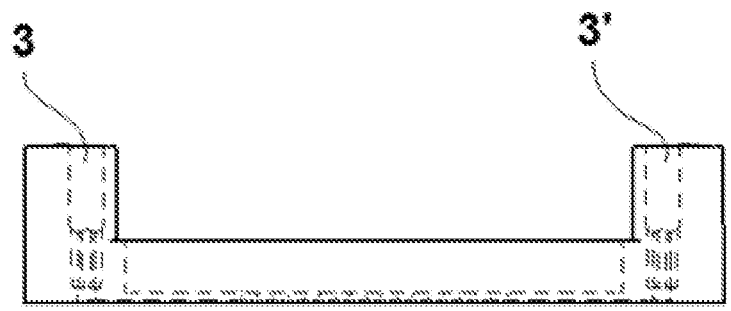
FIGS. 1a and 1b of the present document show, respectively, an elevational view and a top view of the device of the invention, in a preferred embodiment of said device in which three capillary channels are used, and in which each channel communicates nine three-dimensional culture wells.

DESCRIPTION OF THE REFERENCE NUMBERS IN THE DRAWINGS (1) Microfluidic channels.
(2) Three-dimensional (3D) culture wells.
(3, 3') Microfluidic inlet and outlet ports.
(4) Upper region for accessing the wells for two-dimensional (2D) culture.
(5) Walls for confining the upper region for accessing the wells.
(6) Closure cover of the microfluidic system.
(7) Fluidic channels of the closure cover.
(8, 8') Closure cover inlet and outlet ports.

DETAILED DESCRIPTION OF THE INVENTION

A detailed description of the invention is provided below in reference to a preferred embodiment thereof based on FIGS. 1 to 6 of the present document. Said embodiment is provided for illustrative and non-limiting purposes.

Figure 1B:
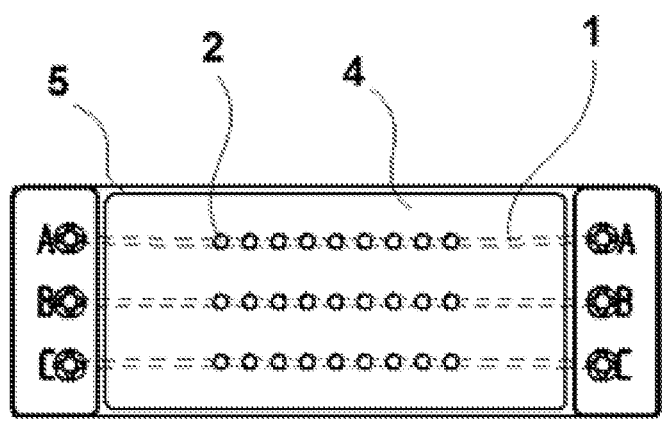

FIGS. 1a and 1b show an elevational view and a top view of a cell culture device in which its main elements are shown. The device preferably comprises one or more channels (1) for circulating cells and/or fluid media, for example, media suitable for cell culture. Each of said channels (1) is connected to a plurality of culture wells (2) forming cell housing volumes in which three-dimensional culture assays can be performed. Therefore, when cells or fluids are circulated through each channel (1), they will occupy the culture volumes as they enter the wells (2).

Figure 2:
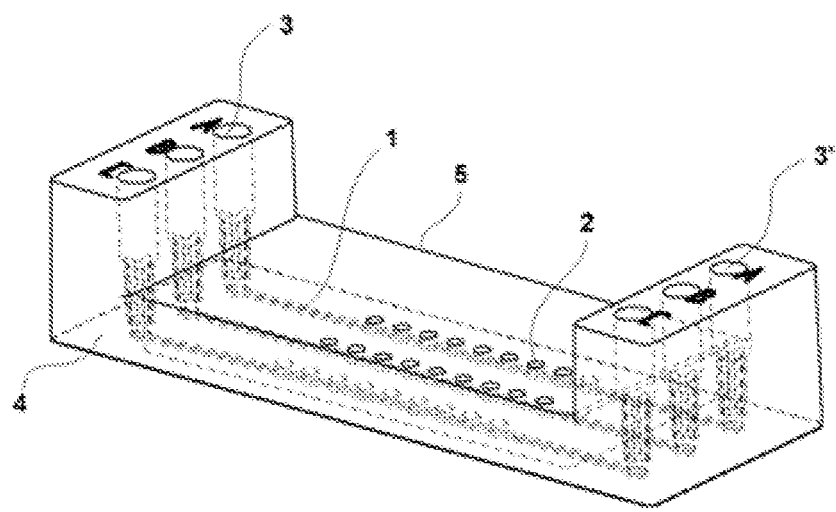
FIG. 2 shows a perspective view of the device of FIGS. 1a and 1b, including the internal detail of its components (channels and inlet/outlet ports).
Figure 3:
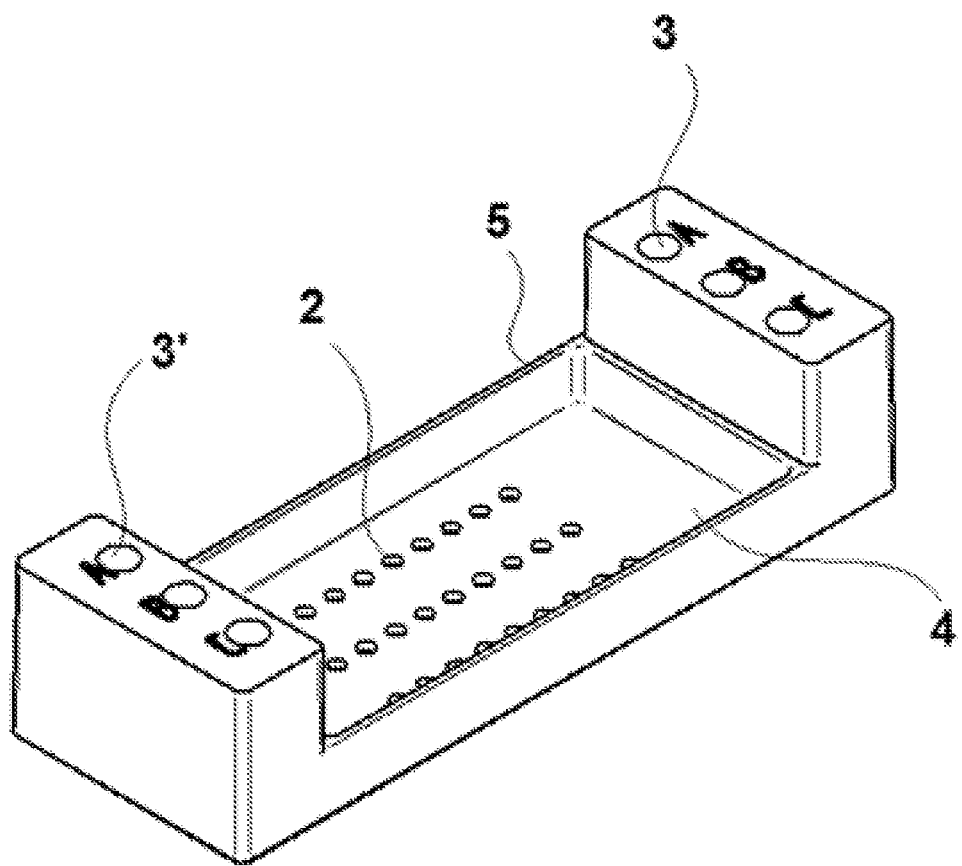
FIG. 3 shows an outer perspective view of the device of FIGS. 1a and 1b.

FIGS. 1 to 3 of the present document show an embodiment of the device in which the wells (2) are arranged in the upper region of the channels (1). Nevertheless, other embodiments also allow the opposite configuration with the wells (2) being located in a lower area.

Additionally, the device of the invention comprises an inlet port (3) and an outlet port (3') connected to the ends of each channel (2). Said ports (3, 3') preferably have the capacity to be used for seeding cells in the device, as well as for causing a flow in the device by means of circulating a fluid therein. The seeding process is preferably performed with a pipette that will fit in the inlet port (3), and will in turn allow the exit of gases, thereby limiting the possibility of introducing bubbles into the system. Furthermore, the upper portion of the fluidic inlet of the port (3) can also be coupled to a tube, thereby allowing a flow to be caused in the device.

The inlet ports (3) of the device allow generating a completely planar interface between the extracellular matrix and the culture medium. These inlet ports (3) are located, like a pressure cylinder, on the level of the culture wells (2), and preferably hold a volume of liquid of at least 25 µl. This liquid column applies hydrostatic pressure on the interface generated in these wells (2), which keeps said interface in its completely planar position, thereby preventing any type of retraction.

In a preferred embodiment of the invention, the channels (1) follow a curved trajectory in the device, and their cross-section has a diameter comprised between 300 and 500 microns. In turn, the wells (2) will preferably have a diameter greater than the diameter of the section of the channels (1).

The cross-section of the channel (1) circulating between the wells (2) favors the occurrence of capillary forces which allow filling the fluidic circuit in a few seconds without having to use pumps. This phenomenon also takes place very rapidly with viscous liquids, such as non-polymerized hydrogels. For this reason, the section of the channel (1) cannot be less than 300 microns for these liquids, thereby preventing the hydrogel from blocking the channel (1) during the polymerization process due to the small volume of hydrogel and the rapid tempering thereof in said case.

The device of the invention also comprises an upper region (4) for accessing the wells (2) configured as an open chip that allows applying a fluid medium in said upper region (4), where it can be used as mechanical stimulation for the cultured cells. The device of the invention thereby allows at least three main modes of operation: surface (2D) behavior analysis of cells in different substrates (when fluid media are applied to the upper region (4)), three-dimensional (3D) cell culture analysis in the wells (2), and finally, a combined 2D and 3D culture analysis, given the open nature of the wells (2) which are also accessible from the upper region (4) of the device. The capacity of the device to work in 2D mode, 3D mode, and in a combination of both modes, allows studying complex multicellular processes, the conditions of which can be replicated inside the device. An example for the application of these techniques would consist of studying tissue invasion by tumor cell cultures in a three-dimensional matrix, or the simulation of complex cellular microenvironments, such as kidney microtubules or pancreatic islets, for example. Other studies that can be performed by means of the device of the invention are, for example, analysis of the topography of fixed cells, measurements of gel rigidity, microstructure topography of circulating gels, etc.

In a preferred embodiment of the device, said device also comprises a plurality of walls (5) confining the perimeter of the upper region (4), which allows using said region (4) to house a small volume of culture medium. This allows taking atomic force microscopy measurements in a living cell in equipment with characteristics suitable to that end. Said measurements include topography, cell-protein adhesion assays, cell-cell adhesion assays in different conditions, mechanical cell stimulation, or measurements related to hydrogels in a liquid medium, most relevant for the characterization thereof.

Other microscopy measurements, for example by means of fluorescence microscopy, confocal laser microscopy, or electron microscopy, can also be taken in the device of the invention. Additionally, since the wells (2) are exposed, the hydrogels can also be removed by means of specific punching with a plunger, for example. This allows the subsequent analysis of the cells immersed in the matrix, if desired.

The embodiments of the device of the invention can preferably be carried out by means of a design consisting of several layers of biocompatible polymeric materials (for example, PDMS, SU-8, etc.) defining the channels (1) and the open wells (2), the filling of which will be performed, as described, by means of perfusion using capillary forces. In this sense, the design of the device of the invention makes it easy to handle since the wells (2) are automatically perfused in a matter of microseconds. The different layers of material of the device can be made, for example, by means of photolithography or injection molding.

Another object of the present invention relates to a microfluidic system for studying cell cultures comprising the device described in the preceding paragraphs, in combination with a closure cover (6) that can be coupled on the upper region (4) of said device. The device of the invention therefore acts as a base support part of the system, and the mentioned closure cover (6) acts as a closure thereof.

Figure 4A:
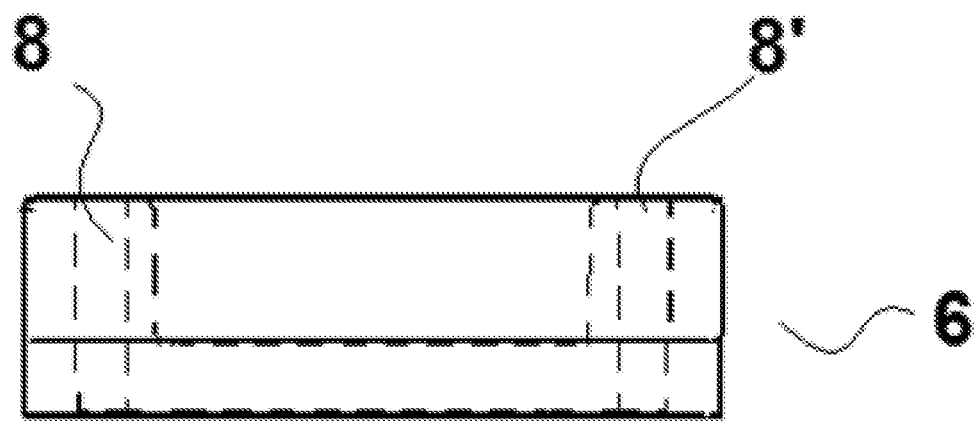
FIGS. 4a and 4b show, respectively, an elevational view and a top view of the closure cover of the invention, according to a preferred embodiment thereof.
Figure 4B:
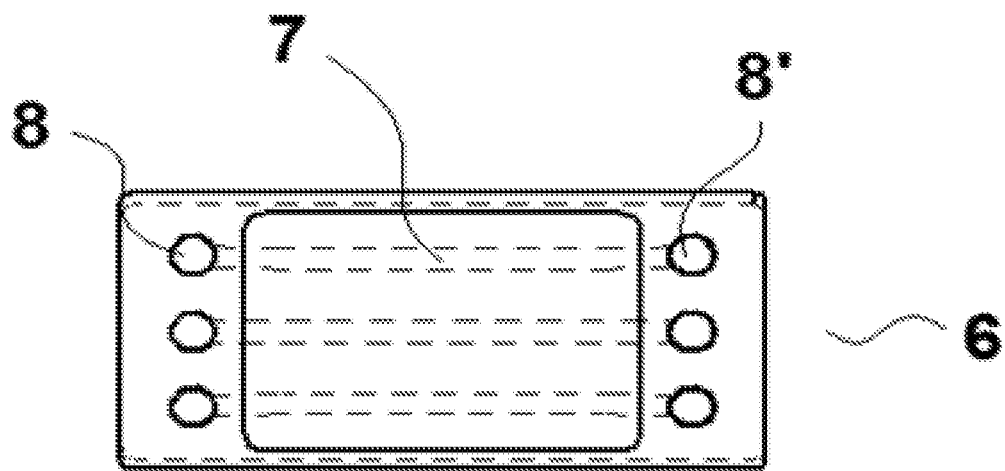
Figure 5:
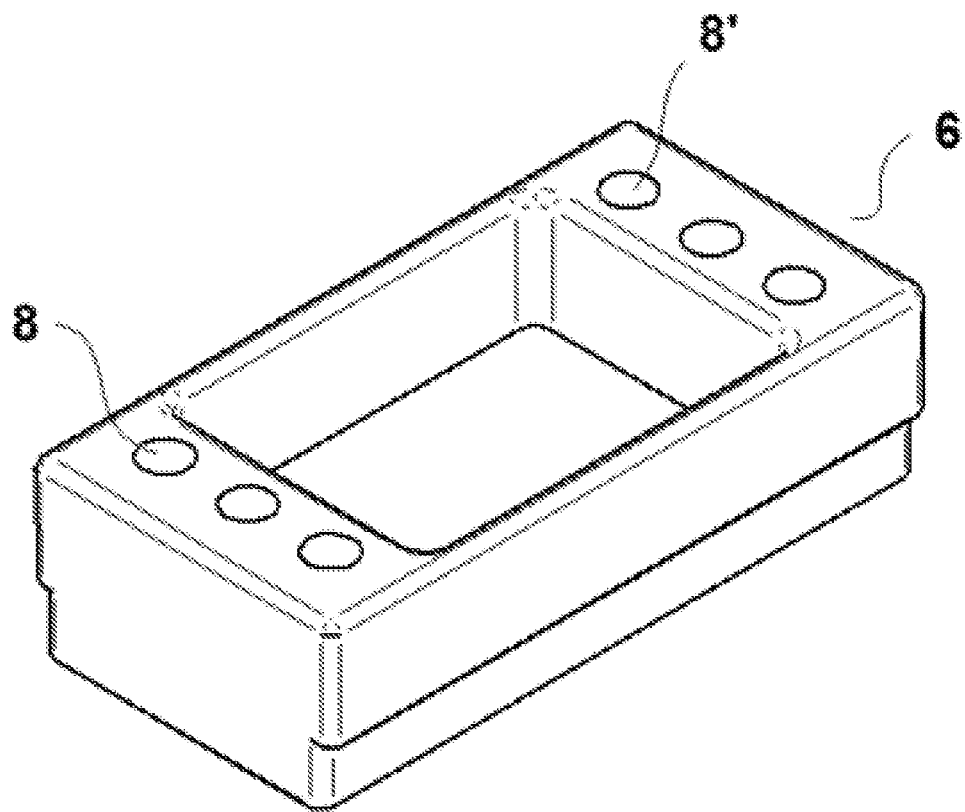
FIG. 5 shows a perspective view of the device of FIGS. 4a and 4b, including the internal detail of its components.
Figure 6:
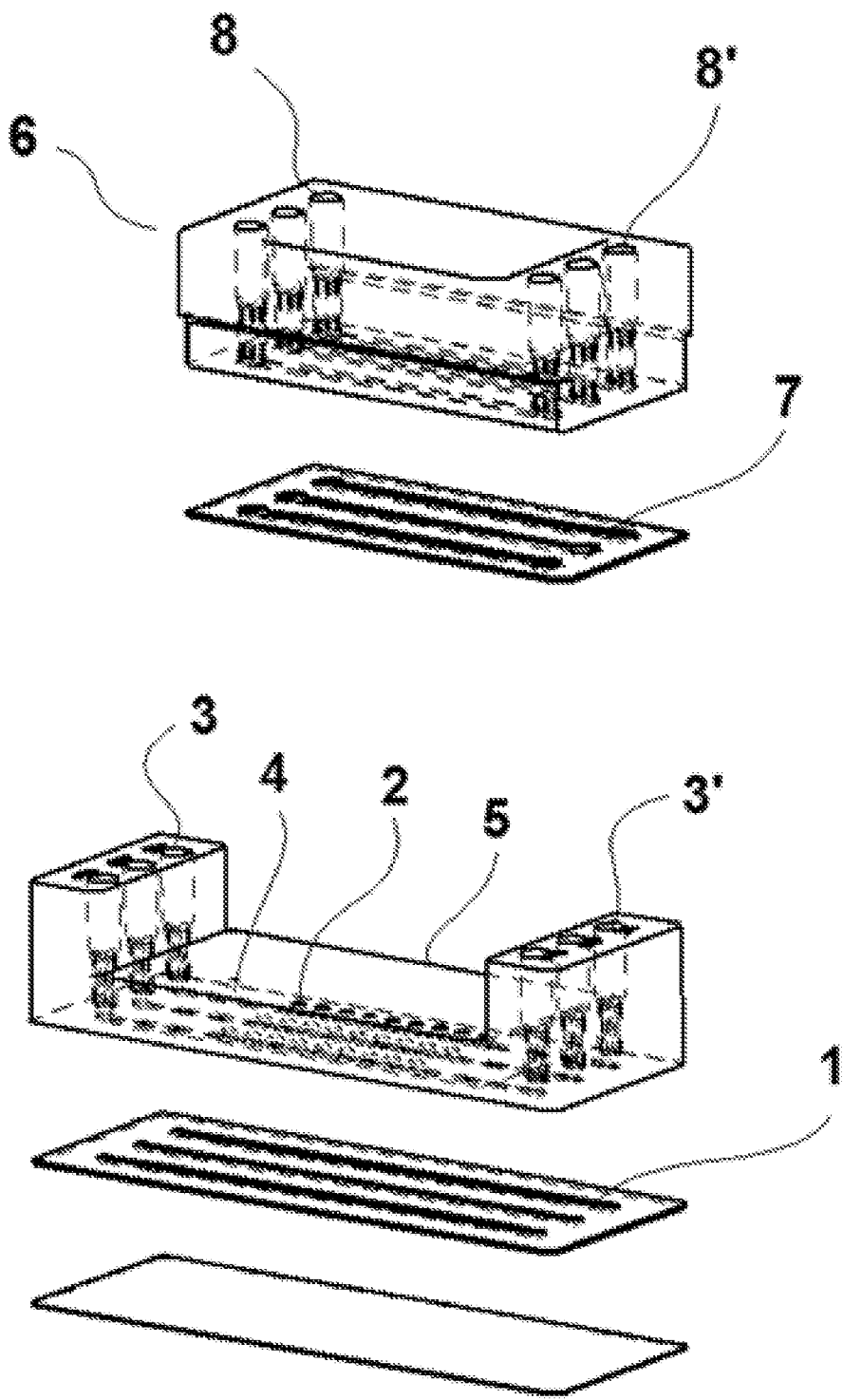
FIG. 6 shows a perspective view, detailing the layers of the system of the invention (showing both the microfluidic device and the closure cover), according to a preferred embodiment of said system.

A preferred embodiment of the closure cover (6) of the invention is shown in FIGS. 4 to 6 of the present document. Said drawings show how said cover (6), like the microfluidic device to which it is coupled, comprises a plurality of fluidic channels (7) having a distribution coinciding with the wells (2) thereof. Therefore when its closure elements are applied on the upper region (4) of the device, the closure cover (6) provides a plurality of surface culture (two-dimensional or 2D) matrices in the spaces immediately above the wells (2), thereby being communicated with them.

Additionally, in order to introduce cells and fluid media in the surface chambers, the closure cover (6) comprises a plurality of fluidic inlet and outlet ports (8, 8') connected to each channel (7). The system of the invention thereby allows performing 3D culture analysis (in the wells (2)), 2D culture analysis (in the upper spaces formed in the interface of the upper accesses with the closure cover (6)), or a combination of both, thereby allowing combined 2D and 3D analyses.

When the system is closed (by means of applying the closure part (6) on the device which works as a base part), the culture spaces are enclosed and configured with their corresponding 3D culture chambers and 2D culture surfaces.

According to the assays to be performed, the inverse perfusion of the matrices in the system of the invention is also feasible. In other words, the upper channel (7) (usually intended for a flow) can be perfused with a hydrogel of the user's choice. That is possible due to the bifunctional pipette-connector inlets (3, 3', 8, 8') of the device and the system of the invention. The hydrogel would therefore be confined in the upper portion of the device. Once the hydrogel has polymerized in the upper portion of the system, a cell suspension can be pipetted through the ports (3, 3') and channels (1) of the lower part, filling the volume intended for the wells (2). Subsequently by turning the device over, a monolayer can be seeded on the gel interface located in said wells (2). Accordingly, once the cells have adhered, a flow can be applied through the lower channels (1).

Performing the assay inversely allows studying the cell monolayer in detail. That is due to the fact that it is closer to the base of the system, so the working distance is considerably reduced. This enables the use of microscope objectives of very high magnification which have a very short working distance. Very high resolution images of the monolayer cells could thus be obtained.

Performing the assay inversely also facilitates other methods. For example, by removing the lower layer of the device (for example, an adhered layer of polystyrene), the monolayer can be left exposed, thereby facilitating the performance of immunofluorescence or atomic force microscopy assays in a fixed cell, among other applications.

The invention claimed is:

1. A microfluidic device for culturing cell samples comprising:
   one or more capillary channels for circulating cells or fluid media, or both, each capillary channel extending between a first end and a second end,
   a first inlet port connected to each first end and a second inlet port connected to each second end for seeding cells or for circulating fluid, or both, through the one or more capillary channels, one or more culture wells forming cell housing volumes for three-dimensional cell culture, wherein the one or more culture wells are formed in the one or more capillary channels such that said one or more capillary channels are connected to the one or more culture wells as culture well perfusion means;

wherein each of the first and second inlet ports have housing volumes for housing a liquid at a level above the level of the one or more capillary channels, such that said liquid exerts pressure at both ends of said one or more capillary channels; and wherein the device further comprises:

an upper region reservoir for containing fluids above the one or more capillary channels and for accessing the one or more culture wells, providing a two-dimensional cell culture surface adjacent thereto, and one or more walls confining a perimeter of the upper region reservoir for containing fluids in said upper region reservoir, and wherein the one or more culture wells are open such that the one or more culture wells are accessible through the upper region reservoir, and wherein each of the first and second inlet ports of the one or more capillary channels extend also above the upper region, and each of the first and second inlet ports have an opening configured such that a pipette or a fluid connector can be fitted therein.

2. The device according to claim 1, wherein each of the first and second inlet ports have a housing volume of at least 25 µl.

3. The device according to claim 1, wherein the one or more capillary channels together with the respective first and second inlet ports, configure a curved trajectory in the device, and a cross-section of the one or more capillary channels has a diameter comprised between 300 and 500 microns.

4. The device according to claim 1, wherein each capillary channel has two or more culture wells arranged in a row within the capillary channel in which they are formed.

5. The device according to claim 1, wherein the device is obtained from one or more biocompatible polymeric materials.

6. The device according to claim 1, wherein each of the one or more culture wells has a diameter larger than the diameter of a section of the capillary channel to which the one or more culture wells are connect.

7. A microfluidic system for studying cell cultures, comprising a device according to claim 1, in combination with a closure cover for enclosing the upper region of said device.

8. The system according to claim 7, wherein the closure cover comprises a plurality of fluidic capillary channels, the layout of which coincides with the distribution of the one or more wells of the microfluidic device.

9. The system according to claim 7, wherein the closure cover comprises a plurality of fluidic inlet and outlet ports connected to each of the one or more capillary channels, wherein the ports comprise housing volumes for housing a liquid at a level different from the level of the one or more capillary channels, said volumes acting like pressure cylinders on said one or more channels.

10. The system according to claim 8, wherein the closure cover comprises a plurality of fluidic inlet and outlet ports connected to each of the one or more capillary channels, wherein the ports comprise housing volumes for housing a liquid at a level different from the level of the one or more capillary channels, said volumes acting like pressure cylinders on said one or more channels.

* * * * *